US012559453B2

(12) United States Patent
Yin et al.

(10) Patent No.: US 12,559,453 B2
(45) Date of Patent: Feb. 24, 2026

(54) SULFONIC ACID-MODIFIED POLYISOCYANATE AND PREPARATION METHOD THEREFOR

(71) Applicant: WANHUA CHEMICAL GROUP CO., LTD., YEDA Yantai (CN)

(72) Inventors: Xundi Yin, YEDA Yantai (CN); Xueshun Ji, YEDA Yantai (CN); Yunquan Jin, YEDA Yantai (CN); Cuicui Wang, YEDA Yantai (CN); Rubao Shen, YEDA Yantai (CN); Yuyang Cao, YEDA Yantai (CN)

(73) Assignee: WANHUA CHEMICAL GROUP CO., LTD., YEDA Yantai (CN)

(*) Notice: Subject to any disclaimer, the term of this patent is extended or adjusted under 35 U.S.C. 154(b) by 579 days.

(21) Appl. No.: 18/003,965

(22) PCT Filed: Apr. 8, 2022

(86) PCT No.: PCT/CN2022/085827
§ 371 (c)(1),
(2) Date: Dec. 30, 2022

(87) PCT Pub. No.: WO2022/257585
PCT Pub. Date: Dec. 15, 2022

(65) Prior Publication Data

US 2023/0257344 A1 Aug. 17, 2023

(30) Foreign Application Priority Data

Jun. 11, 2021 (CN) ........................ 202110650822.4

(51) Int. Cl.

| | |
|---|---|
| ***C08G 18/20*** | (2006.01) |
| ***C07C 303/22*** | (2006.01) |
| ***C07C 309/26*** | (2006.01) |
| ***C08G 18/24*** | (2006.01) |
| ***C08G 18/38*** | (2006.01) |
| ***C08G 18/77*** | (2006.01) |

(52) U.S. Cl.
CPC .......... *C07C 309/26* (2013.01); *C07C 303/22* (2013.01); *C08G 18/20* (2013.01); *C08G 18/2009* (2013.01); *C08G 18/244* (2013.01); *C08G 18/3855* (2013.01); *C08G 18/775* (2013.01)

(58) Field of Classification Search
CPC ................ C08G 18/20; C08G 18/2009; C08G 18/244; C08G 18/775; C08G 18/3855
See application file for complete search history.

(56) References Cited

U.S. PATENT DOCUMENTS

| | | | | |
|---|---|---|---|---|
| 5,202,377 | A | 4/1993 | Thorne et al. | |
| 6,767,958 | B2 | 7/2004 | Laas et al. | |
| 9,975,985 | B2 | 5/2018 | Ji et al. | |
| 11,365,277 | B2 | 6/2022 | Laas | |
| 2016/0280836 | A1* | 9/2016 | Ji | C08G 18/8083 |
| 2021/0130530 | A1* | 5/2021 | Laas | C08G 18/7621 |
| 2021/0171698 | A1* | 6/2021 | Laas | C08G 18/288 |

FOREIGN PATENT DOCUMENTS

| | | | |
|---|---|---|---|
| CN | 1429240 | | 7/2003 |
| CN | 104448232 | | 3/2015 |
| CN | 110092887 | | 8/2019 |
| CN | 110387030 | | 10/2019 |
| CN | 111517994 | | 8/2020 |
| CN | 112041369 | | 12/2020 |
| CN | 112062935 | | 12/2020 |
| EP | 2218740 | A1 | 8/2010 |
| EP | 2236532 | A1 | 10/2010 |
| EP | 3045485 | A1 | 7/2016 |
| WO | 0188006 | A1 | 11/2001 |
| WO | WO2020109189 | | 6/2020 |

OTHER PUBLICATIONS

European Search Report issued for Application No. 22809633.5, mailed Mar. 5, 2024.
PCT Search Report and Written Opinion prepared for PCT Application No. PCT/CN2022/085827, completed Jun. 8, 2022.

* cited by examiner

*Primary Examiner* — Michael L Leonard
(74) *Attorney, Agent, or Firm* — Barnes & Thornburg LLP

(57) ABSTRACT

Disclosed are a sulfonic acid-modified polyisocyanate and a preparation method thereof. By controlling a content of cyclohexylamine component in the raw material, the reaction rate of sulfamic acid and polyisocyanate is accelerated, so that the prepared product has advantages of light color and low turbidity as well as good storage stability.

20 Claims, No Drawings

SULFONIC ACID-MODIFIED POLYISOCYANATE AND PREPARATION METHOD THEREFOR

CROSS-REFERENCE TO RELATED APPLICATIONS

This application is a national stage entry under 35 USC § 371(b) of PCT International Application No. PCT/CN2022/085827, filed Apr. 8, 2022, which claims priority to Chinese Patent Application Serial Number 202110650822.4, filed on Jun. 11, 2021, the entire disclosures of both of which are incorporated herein by reference.

TECHNICAL FIELD

An embodiment of the present application relates to the field of modified isocyanates, such as a hydrophilic sulfonic acid-modified polyisocyanate and a preparation method thereof. An embodiment of the present application also relates to a use of the prepared hydrophilic sulfonic acid-modified polyisocyanate in the fields of coating agents, adhesives, sealants and the like.

BACKGROUND

With the increasing pressure of environmental protection, water-based coatings and adhesive compositions have become the best environmentally friendly alternatives to solvent-based coatings and adhesives. However, the introduction of hydrophilic components and the production process determine their water resistance, solvent resistance and heat resistance are poor, while the introduction of water-based isocyanate curing agents can effectively improve the resistance of water-based coatings and adhesives.

Water-based isocyanate curing agents can be divided into two categories according to their hydrophilic groups: one is the polyether-modified isocyanate curing agent, and the other is the sulfonic acid-modified isocyanate curing agent. In those two categories, although the polyether-modified isocyanate curing agent has gained widespread acceptance by the market, its application is limited by some inherent shortcomings, such as low effective isocyanate content and poor resistance, caused by the high polyether content which is introduced for good hydrophilicity. The sulfonic acid-modified isocyanate curing agent has increasingly wide application due to the advantages of high functionality and easy dispersion.

Patent CN1190450C adopts 3-(cyclohexylamino)propanesulfonic acid and 2-(cyclohexylamino)ethanesulfonic acid solid powders to prepare a sulfonic acid-modified polyisocyanate, and the obtained modified polyisocyanate can be dispersed evenly in water without high shear force. CN104448232B adopts 4-(cyclohexylamino)ethanesulfonic acid solid powders to prepare a sulfonic acid-modified polyisocyanate, and also obtains a sulfonic acid-modified polyisocyanate with excellent performance However, the methods of modifying isocyanate curing agent with solid sulfonic acid compound in related art has certain defects: firstly, the compatibility of sulfonic acid solid powders with isocyanate is poor, and the interface reaction leads to long reaction time and deep product color; secondly, the incomplete reaction of solid powders will cause high turbidity of product and deepen the color with the extension of storage time.

SUMMARY

The following is a summary of the subject detailed in the present disclosure. The summary is not intended to limit the protection scope of the claims.

In an embodiment, the present application provides a sulfonic acid-modified polyisocyanate and a preparation method thereof, which can effectively improve the shortcomings of the related method of sulfonic acid-modified isocyanate, such as slow reaction rate, high product turbidity, and easy deepening of storage color, and thus ensures a fast reaction rate, low product turbidity, and good storage stability.

In an embodiment, the present application provides a sulfonic acid-modified polyisocyanate, which is a reaction product obtained from a reaction including the following components:

a) at least one polyisocyanate component;

b) at least one organic compound with one or more of a sulfonic acid group and/or a sulfonate group, in which the compound contains at least one of a mercapto group, a primary amino group or a secondary amino group;

c) at least one tertiary amine;

d) at least one cyclohexylamine with the following structure:

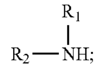

wherein, $R_1$ is one of cyclohexyl, cyclohexylmethyl, p-methylcyclohexyl, 2-methylcyclohexyl, 2,3-dimethylcyclohexyl, 3,3,5-trimethylcyclohexyl or 4-tert-butylcyclohexyl, and $R_2$ is hydrogen or a saturated or unsaturated, linear or branched, aliphatic or alicyclic, or aromatic organic group having 1 to 18 carbon atoms.

Preferably, based on a mass of the component a) being 1000 parts, a mass of the component b) added is 5-150 parts, preferably 15-120 parts.

Preferably, a molar ratio of the component c) to the component b) is 0.5-1.5:1. Preferably, the component a) of polyisocyanate is one or more of an aliphatic polyisocyanate, a alicyclic polyisocyanate, an araliphatic polyisocyanate and/or an aromatic polyisocyanate, or a modified polyisocyanate, which has an average isocyanate functionality of 2.0-5.0 and an NCO content of 7.0-32.0 wt %.

The above modified polyisocyanate can be the modified polyisocyanate containing a structure of uretdione, isocyanurate, allophanate, biuret, iminooxadiazinedione and/or oxadiazinetrione, which can be prepared from one or more of an aliphatic diisocyanate, a alicyclic diisocyanate, an aromatic diisocyanate and/or an araliphatic diisocyanate, and the methods in patents can be used in modifying and preparing, such as DE1670666A, DE1954093A, DE2414413A, DE2452532A, DE2641380A, DE3700209A, DE3900053A, DE3928503A, EP0336205A, EP0339396A and EP0798299A.

Suitable diisocyanates for preparing the above modified polyisocyanate containing a structure of uretdione, isocyanurate, allophanate, biuret, iminooxadiazinedione and/or oxadiazinetrione can be those obtained by the phosgene or non-phosgene process, for example, any diisocyanate obtained by thermal decomposition of urethane.

Preferably, the polyisocyanate is an aliphatic, alicyclic, araliphatic or aromatic diisocyanate which has a molecular mass of 100-500, such as tetramethylene diisocyanate, pentamethylene diisocyanate, hexamethylene diisocyanate, dodecamethylene diisocyanate, 1,4-cyclohexane diisocyanate, isophorone diisocyanate, 4,4'-dicyclohexylmethane diisocyanate, 4,4'-dicyclohexylpropane diisocyanate, 1,4-phenylene diisocyanate, 2,4-toluene diisocyanate, 2,6-toluene diisocyanate, 4,4'-diphenylmethane diisocyanate, 2,2'-diphenylmethane diisocyanate, 2,4'-diphenylmethane diisocyanate, tetramethyl-xylylene diisocyanate and p-xylylene diisocyanate, or a mixture of the diisocyanates.

Preferably, the polyisocyanate is a modified polyisocyanate with an isocyanurate group based on one or more of 1,6-hexamethylene diisocyanate (HDI), isophorone diisocyanate (IPDI) and 4,4'-dicyclohexylmethane diisocyanate ($H_{12}MDI$).

An antioxidant, a free radical scavenger or an inhibitor can be added during the preparation of the above modified polyisocyanate containing a structure of uretdione, isocyanurate, allophanate, biuret, iminooxadiazinedione and/or oxadiazinetrione.

Preferably, the component b) is a sulfonic acid and/or a sulfonate, which has an amino group, and the component b) is preferably a sulfonic acid and/or a sulfonate, which has a secondary amino group.

Furthermore, the component b) is a sulfonic acid organic compound with a secondary amino group, which has the following structure:

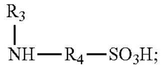

wherein, $R_3$ is one of cyclohexyl, cyclohexylmethyl, p-methylcyclohexyl, 2-methylcyclohexyl, 2,3-dimethylcyclohexyl, 3,3,5-trimethylcyclohexyl or 4-tert-butylcyclohexyl, and $R_4$ is a linear or branched aliphatic group having 2 to 6 carbon atoms.

The component b) can be partially or completely neutralized into a salt by the tertiary amine c) before the reaction, during the reaction and/or after the reaction. On the one hand, the tertiary amine is used to neutralize the sulfonic acid/or sulfonate group in the component b) to form a sulfonate; on the other hand, the tertiary amine also catalyze the reaction of polyisocyanate and sulfamic acid as a phase transfer catalyst.

The tertiary amine c) is an acyclic and/or cyclic tertiary amine substituted with an aliphatic and/or alicyclic group, and the tertiary amine c) is optionally one or more of trimethylamine, triethylamine, tripropylamine, N,N-dimethylbutylamine, N,N-diethylmethylamine, N,N-diisopropylethylamine, N,N-dimethylcyclohexylamine, N-methylpiperidine, N-methylquinoline, N-ethylquinoline and/or N-ethylmorpholine, or other tertiary amine in the art which is used to catalyze the reaction of the polyisocyanate component and the component b), preferably N,N-dimethylcyclohexylamine Preferably, a catalyst, conventionally used in the polyurethane field, is further added in the modified polyisocyanate to mix with the tertiary amine c) for use, such as an organometallic catalyst: one or a mixture of at least two of aluminium tris(ethyl acetoacetate), tin n-octoate, zinc n-octoate, tin(II) 2-ethyl-1-hexanoate, dibutyltin(IV) dichloride, dibutyltin(IV) diacetate, dibutyltin(IV) dilaurate, dioctyltin (IV) diacetate or molybdenum glycolate.

Preferably, the component d) of cyclohexylamine is one or more of cyclohexylamine, cyclohexanemethylamine, p-methylcyclohexylamine, 2-methylcyclohexylamine, 2,3-dimethylcyclohexylamine, 3,3,5-trimethylcyclohexylamine, 4-tert-butylcyclohexylamine, N-methylcyclohexylamine, N-methyl-cyclohexylmethylamine, N,4-dimethylcyclohexan-1-amine, N-methyl-2-methylcyclohexylamine, N-methyl-2,3-dimethylcyclohexylamine, N-methyl-3,3,5-trimethylcyclohexylamine, N-methyl-4-tert-butylcyclohexylamine, N-ethylcyclohexylamine, N-ethyl-methylcyclohexylamine, N-ethyl-p-methylcyclohexylamine, N-methyl-2-methylcyclohexylamine, N-ethyl-2,3 -dimethylcyclohexylamine, N-methyl-3,3,5-trimethylcyclohexylamine, and N-ethyl-4-tert-butylcyclohexylamine.

Preferably, based on a mass of the component a) being 1000 parts, a mass of the component d) added is 0.05-2 parts, preferably 0.2-1.6 parts. The applicant of the present application surprisingly found that when the content of the added component d) is controlled within a certain range, the compatibility of sulfamic acid with polyisocyanate can be effectively improved, the reaction rate can be accelerated, the turbidity of the obtained product is low, and the storage stability is good. The amount of component d) of cyclohexylamine is too small to improve the compatibility of sulfamic acid with polyisocyanate; and the amount of component b) is too much to react with polyisocyanate too quickly, which will easily form a highly viscous layer on the surface of component b) particles and prevent component b) from further dissolution and reaction.

In order to better increase the compatibility of sulfamic acid with polyisocyanate, accelerate the reaction rate, and obtain a product with light color and low turbidity, preferably, the component d) of cyclohexylamine contains cyclohexylamine having the same group as $R_3$ in the component b) of organic compound.

The present application also relates to a preparation method of the sulfonic acid-modified polyisocyanate, including reacting the component a) of polyisocyanate component, the component b) and the component d) at 70-110° C. in the presence of the component c) of tertiary amine, wherein the component a) of polyisocyanate is optionally fed in one or more steps. During the preparation process, an antioxidant can be added to reduce the color number. The antioxidant can be an aromatic amine, a hindered phenol, and a derivative thereof, which can scavenge free radicals, or a phosphorus-containing or sulfur-containing organic compound which can enable the decomposition of hydroperoxides, or a combination thereof.

In the method of the present application, the reaction is optionally carried out in a solvent which is inert to reacting with NCO. For example, the solvent is one or a mixture of at least two of acetone, butanone, ethyl oxocyclopentylacetate, butyl acetate, N-ethylpyrrolidone, N-methylpyrrolidone, toluene, xylene, chlorobenzene, propylene glycol methyl ether acetate, 1-methoxyprop-2-yl acetate, 3-methoxy-n-butyl acetate, an aromatic compound, dimethyl carbonate, diethyl carbonate, butyrolactone, caprolactone and methyl caprolactone.

The present application also provides a use of the hydrophilic sulfonic acid-modified polyisocyanate and the modified polyisocyanate prepared by the method of the present application as a crosslinking agent in two-component water-dispersible coatings and adhesives. They have light color, low turbidity, excellent storage stability at room temperature and excellent water dispersibility.

The present application also provides a use of the hydrophilic sulfonic acid-modified polyisocyanate as a starting component in preparing a blocked polyisocyanate which is water-dispersible or exists as a dispersion in water. A suitable blocking agents is, for example, diethyl malonate, ethyl acetoacetate, 3,5-dimethylpyrazole, imidazole, and ε-caprolactam, or a mixture of these blocking agents.

In addition to being used as cross-linking component in two-component coatings and adhesives, the sulfonic acid-modified polyisocyanate of the present application can also be used as a cross-linking agent in fabric finishing, adhesives for printing coatings, and crosslinking other aqueous dispersions, or be used as an auxiliary in moisturizing paper.

In the present application, by introducing cyclohexylamine into polyisocyanate, the compatibility of polyisocyanate with the organic compound with at least one sulfonic acid group and/or sulfonate group is increased, the reaction rate is accelerated, and the hydrophilic sulfonic acid-modified polyisocyanate product with light color and low turbidity is also obtained when the production efficiency is greatly increased.

Other aspects will become apparent upon reading and understanding the detailed description.

DETAILED DESCRIPTION

The present application will be further described below with reference to the embodiments. It should be noted that the embodiments have no limitation on the protection scope of the present application.

- Polyisocyanate a1: (Wanhua Chemical Wannate® HT-100, the polyisocyanate based on HDI, NCO=21.7-22.2 wt %);
- Polyisocyanate a2: (Bayer NZ1, the polyisocyanate based on HDI and IPDI, NCO=20 wt %)
- Sulfamic acid b1: 2-(cyclohexylamino)ethanesulfonic acid, purchased from Aladdin, purity≥99%
- Sulfamic acid b2: 3-(cyclohexylamino)propanesulfonic acid, purchased from J&K Chemicals, purity 99%
- Sulfamic acid b3: 4-(cyclohexylamino)butanesulfonic acid, which is prepared by reacting cyclohexylamine and 1,4-butanesultone with a molar ratio of 3:1 in dioxane solvent at 80° C. for 6 h, collecting the solid, and washing the solid with acetone to white.
- Sulfamic acid b4: 3-(p-methylcyclohexylamino)propanesulfonic acid, which is prepared by reacting p-methylcyclohexylamine and 1,4-butanesultone with a molar ratio of 3:1 in dioxane solvent at 80° C. for 6 h, collecting the solid, and washing the solid with acetone to white.
- Tertiary amine c1: N,N-dimethylcyclohexylamine, purchased from J&K Chemicals, purity 99%
- Tertiary amine c2: N-ethylmorpholine, purchased from J&K Chemicals, purity 99%
- Primary amine d1: cyclohexylamine, purchased from J&K Chemicals, purity 99%
- Primary amine d2: 4-methylcyclohexylamine, purchased from J&K Chemicals, purity 95%
- Primary amine d3: cyclohexylmethylamine, purchased from J&K Chemicals, purity 98%
- Secondary amine d4: N-methylcyclohexylamine, purchased from J&K Chemicals, purity 98%
- Secondary amine d5: N-ethylcyclohexylamine, purchased from J&K Chemicals, purity 99%

Testing method:

1. NCO determination standard: GB/T 12009.4-2016
2. Viscosity test standard: Brookfield LV 63#/3 rpm, 25° C.
3. Color number test standard: using 723C visible spectrophotometer, and using Hazen scale for measurement
4. Turbidity test standard: using HACH 2100Q Portable Turbidimeter for measurement, in NTU.

Example 1

In a four-neck round-bottom flask equipped with a mechanical stirrer, a reflux condenser, a thermometer, and nitrogen inlet and outlet, 0.32 g of cyclohexylamine d1 (0.003 mol) was added dropwise to 380 g of polyisocyanate al at 50° C. with stirring at 200 rpm, and reacted for 10 min, then 17.39 g (0.084 mol) of sulfamic acid b1 and 10.67 g (0.084 mol) of tertiary amine c1 were added to the reaction system, mixed uniformly, heated to 80° C. and reacted for 3 h, then the reaction was stopped, and the product was filtered through a 325 mesh filter screen, and cooled to room temperature to obtain a sulfamic acid-modified polyisocyanate with the following characteristic data:

solid content: 100%;
NCO content: 19.5 wt %;
average NCO functionality: 3.39;
viscosity (25° C.): 5600 mPa·s;
$SO_3$_ content: 1.65 wt %;
color number: 6; and
turbidity: 0.2.

Example 2

In a four-neck round-bottom flask equipped with a mechanical stirrer, a reflux condenser, a thermometer, and nitrogen inlet and outlet, 17.39 g (0.084 mol) of sulfamic acid b1 and 6.4 g (0.042 mol) of tertiary amine c1 were added to 380 g of polyisocyanate a1, stirred at 200 rpm, mixed uniformly, and heated to 80° C., 0.6 g (0.006 mol) of cyclohexylamine d1 was added dropwise to the reaction system and reacted for 3 h, then the reaction was stopped, and the product was filtered through a 325 mesh filter screen, and cooled to room temperature to obtain a sulfamic acid-modified polyisocyanate with the following characteristic data:

solid content: 100%;
NCO content: 19.59 wt %;
average NCO functionality: 3.39;
viscosity (25° C.): 5500 mPa·s;
$SO_3$_ content: 1.66 wt %;
color number: 4; and
turbidity: 0.

Example 3

In a four-neck round-bottom flask equipped with a mechanical stirrer, a reflux condenser, a thermometer, and nitrogen inlet and outlet, 17.39 g (0.084 mol) of sulfamic acid b1 and 16 g (0.126 mol) of tertiary amine c1 were added to 380 g of polyisocyanate a1, stirred at 200 rpm, mixed uniformly, and heated to 80° C., 0.08 g (0.001 mol) of cyclohexylamine d1 was added dropwise to the reaction system and reacted for 4 h, then the reaction was stopped, and the product was filtered through a 325 mesh filter screen, and cooled to room temperature to obtain a sulfamic acid-modified polyisocyanate with the following characteristic data:

solid content: 100%;
NCO content: 19.40 wt %;
average NCO functionality: 3.40;
viscosity (25° C.): 5500 mPa·s;
$SO_3$_ content: 1.63 wt %;
color number: 14; and
turbidity: 0.6.

Example 4

In a four-neck round-bottom flask equipped with a mechanical stirrer, a reflux condenser, a thermometer, and nitrogen inlet and outlet, 18.57 g (0.084 mol) of sulfamic acid b2 and 10.67 g (0.084 mol) of tertiary amine c1 were added to 380 g of polyisocyanate a1, stirred at 200 rpm, mixed uniformly, and heated to 80° C., 0.32 g (0.003 mol) of cyclohexylamine d1 was added dropwise to the reaction system and reacted for 3 h, then the reaction was stopped, and the product was cooled to room temperature, and filtered through a 325 mesh filter screen to obtain a sulfamic acid-modified polyisocyanate with the following characteristic data:

solid content: 100%;
NCO content: 19.35 wt %;
average NCO functionality: 3.39;
viscosity (25° C.): 5800 mPa·s;
$SO_3$_ content: 1.64 wt %;
color number: 4; and
turbidity: 0.2.

Example 5

The main difference between this example and Example 4 is that the amount of cyclohexylamine d1 added was 0.75 g, and a sulfamic acid-modified polyisocyanate with the following characteristic data was obtained:

solid content: 100%;
NCO content: 19.39 wt %;
average NCO functionality: 3.39;
viscosity (25° C.): 5600 mPa·s;
$SO_3$_ content: 1.64 wt %;
color number: 26; and
turbidity: 1.3.

Example 6

The main difference between this example and Example 4 is that the amount of cyclohexylamine d1 added was 0.60 g, and a sulfamic acid-modified polyisocyanate with the following characteristic data was obtained:

solid content: 100%;
NCO content: 19.45 wt %;
average NCO functionality: 3.39;
viscosity (25° C.): 6000 mPa·s;
$SO_3$_ content: 1.64 wt %;
color number: 9; and
turbidity: 0.2.

Example 7

The main difference between this example and Example 4 is that the mass of cyclohexylamine d1 added was 0.10 g, and a sulfamic acid-modified polyisocyanate with the following characteristic data was obtained:

solid content: 100%;
NCO content: 19.48 wt %;
average NCO functionality: 3.40;
viscosity (25° C.): 5600 mPa·s;
$SO_3$_ content: 1.64 wt %;
color number: 15; and
turbidity: 0.8.

Example 8

The main difference between this example and Example 4 is that the mass of cyclohexylamine d1 added was 0.02 g, and a sulfamic acid-modified polyisocyanate with the following characteristic data was obtained:

solid content: 100%;
NCO content: 19.44 wt %;
average NCO functionality: 3.40;
viscosity (25° C.): 5700 mPa·s;
$SO_3$_ content: 1.64 wt %;
color number: 25; and
turbidity: 1.1.

Example 9

In a four-neck round-bottom flask equipped with a mechanical stirrer, a reflux condenser, a thermometer, and nitrogen inlet and outlet, 18.57 g (0.084 mol) of sulfamic acid b2 and 10.67 g (0.084 mol) of tertiary amine c1 were added to 380 g of polyisocyanate a1, stirred at 200 rpm, mixed uniformly, and heated to 80° C., 0.42 g of cyclohexylamine d5 was added dropwise to the reaction system and reacted for 3 h, then the reaction was stopped, and the product was filtered through a 325 mesh filter screen, and cooled to room temperature to obtain a sulfamic acid-modified polyisocyanate with the following characteristic data:

solid content: 100%;
NCO content: 19.48 wt %;
average NCO functionality: 3.39;
viscosity (25° C.): 5600 mPa·s;
$SO_3$_ content: 1.64 wt %;
color number: 9; and
turbidity: 0.2.

Example 10

In a four-neck round-bottom flask equipped with a mechanical stirrer, a reflux condenser, a thermometer, and nitrogen inlet and outlet, 18.57 g (0.084 mol) of sulfamic acid b2 and 9.66 g (0.084 mol) of tertiary amine c2 were added to 380 g of polyisocyanate a1, stirred at 200 rpm, mixed uniformly, and heated to 80° C., 0.37 g of cyclohexylamine d2 was added dropwise to the reaction system and reacted for 3 h, then the reaction was stopped, and the product was filtered through a 325 mesh filter screen, and cooled to room temperature to obtain a sulfamic acid-modified polyisocyanate with the following characteristic data:

solid content: 100%;
NCO content: 19.5 wt %;
average NCO functionality: 3.39;
viscosity (25° C.): 6000 mPa·s;
$SO_3$_ content: 1.64 wt %;
color number: 7; and
turbidity: 0.2.

Example 11

In a four-neck round-bottom flask equipped with a mechanical stirrer, a reflux condenser, a thermometer, and nitrogen inlet and outlet, 19.75 g (0.084 mol) of sulfamic acid b3 and 10.67 g (0.084 mol) of tertiary amine c1 were added to 380 g of polyisocyanate a2, stirred at 200 rpm, mixed uniformly, and heated to 80° C., 0.38 g of cyclohexylamine d3 was added dropwise to the reaction system and reacted for 5 h, then the reaction was stopped, and the product was filtered through a 325 mesh filter screen, and cooled to room temperature to obtain a sulfamic acid-modified polyisocyanate with the following characteristic data:

solid content: 100%;
NCO content: 17.54 wt %;
average NCO functionality: 3.24;
viscosity (25° C.): 5100 mPa·s;
$SO_3$_ content: 1.64 wt %;
color number: 11; and
turbidity: 0.3.

Example 12

In a four-neck round-bottom flask equipped with a mechanical stirrer, a reflux condenser, a thermometer, and nitrogen inlet and outlet, 9.28 g (0.042 mol) of sulfamic acid b2 and 5.33 g (0.042 mol) of tertiary amine c1 were added to 380 g of polyisocyanate a1, stirred at 200 rpm, mixed uniformly, and heated to 80° C., 0.4 g of cyclohexylamine d4 was added dropwise to the reaction system and reacted for 3 h, then the reaction was stopped, and the product was filtered through a 325 mesh filter screen, and cooled to room temperature to obtain a sulfamic acid-modified polyisocyanate with the following characteristic data:

solid content: 100%;
NCO content: 20.59 wt %;
average NCO functionality: 3.47;
viscosity (25° C.): 3800 mPa·s;
$SO_3$_ content: 0.85 wt %;
color number: 4; and
turbidity: 0.1.

Example 13

In a four-neck round-bottom flask equipped with a mechanical stirrer, a reflux condenser, a thermometer, and nitrogen inlet and outlet, 37.12 g (0.17 mol) of sulfamic acid b2 and 21.33 g (0.17 mol) of tertiary amine c1 were added to 380 g of polyisocyanate a1, stirred at 200 rpm, mixed uniformly, and heated to 80° C., 0.32 g (0.003 mol) of cyclohexylamine dl was added dropwise to the reaction system and reacted for 4 h, then the reaction was stopped, and the product was filtered through a 325 mesh filter screen, and cooled to room temperature to obtain a sulfamic acid-modified polyisocyanate with the following characteristic data:

solid content: 100%;
NCO content: 17.20 wt %;
average NCO functionality: 3.24;
viscosity (25° C.): 7700 mPa·s;
$SO_3$_ content: 3.06 wt %;
color number: 17; and
turbidity: 0.7.

Comparative Example 1

The main difference between this comparative example and Example 4 is that the addition amount of cyclohexylamine d1 was 0.01 g, and a sulfamic acid-modified polyisocyanate with the following characteristic data was obtained:

solid content: 100%;
NCO content: 19.50 wt %;
average NCO functionality: 3.4;
viscosity (25° C.): 5900 mPa·s;
$SO_3$_ content: 1.64 wt %;
color number: 61; and
turbidity: 4.7.

Comparative Example 2

The main difference between this comparative example and Example 4 is that no cyclohexylamine d1 was added during the preparation process, and a sulfamic acid-modified polyisocyanate with the following characteristic data was obtained:

solid content: 100%;
NCO content: 19.44 wt %;
average NCO functionality: 3.4;
viscosity (25° C.): 5300 mPa·s;
$SO_3$_ content: 1.64 wt %;
color number: 82; and
turbidity: 7.2.

Comparative Example 3

The main difference between this comparative example and Example 4 is that the addition amount of cyclohexylamine d1 added was 0.85 g, and a sulfamic acid-modified polyisocyanate with the following characteristic data was obtained:

solid content: 100%;
NCO content: 19.31 wt %;
average NCO functionality: 3.38;
viscosity (25° C.): 6400 mPa·s;
$SO_3$_ content: 1.64 wt %;
color number: 96; and
turbidity: 12.

It can be seen from Examples 1-13 and Comparative Examples 1-2 that, by introducing a small amount of cyclohexylamine into the system, the reaction rate of sulfamic acid and polyisocyanate can be improved, so as to obtain the hydrophilic sulfonic acid-modified polyisocyanate with light color and low turbidity. It can be seen from Comparative Examples 1 and 3 that there is no good effect with too much or too little primary amine introduced, and products with light color and low turbidity cannot be obtained.

Storage stability test: 200 g of the prepared sulfamic acid-modified polyisocyanate is packed into a 250 mL aluminum bottle (heated in a 100° C. oven for 1 h before use), purged with nitrogen for 30 s, then stored in a 50° C. oven, and determined after 30 days for the NCO content, viscosity, and color number. The specific data are shown in the table below.

TABLE 1

Test data of storage stability

| | Initial Indicator | | | After Storage at 50° C. for One Month | | |
|---|---|---|---|---|---|---|
| Sample | Viscosity (25° C. mPa · s) | NCO (%) | Color No. | Viscosity (25° C. mPa · s) | NCO (%) | Color No. |
| Example 1 | 5600 | 19.50 | 6 | 5800 | 19.46 | 7 |
| Example 2 | 5500 | 19.59 | 4 | 5600 | 19.56 | 5 |
| Example 3 | 5500 | 19.40 | 14 | 5400 | 19.37 | 16 |
| Example 4 | 5800 | 19.35 | 4 | 5900 | 19.35 | 6 |
| Example 5 | 5600 | 19.39 | 26 | 5600 | 19.38 | 32 |
| Example 6 | 6000 | 19.45 | 9 | 6100 | 19.40 | 11 |
| Example 7 | 5600 | 19.48 | 15 | 5500 | 19.47 | 18 |
| Example 8 | 5700 | 19.44 | 25 | 5800 | 19.42 | 30 |
| Example 9 | 5600 | 19.48 | 9 | 5600 | 19.43 | 10 |
| Example 10 | 6000 | 19.50 | 7 | 6200 | 19.41 | 9 |
| Example 11 | 5100 | 17.54 | 11 | 5000 | 17.53 | 13 |

TABLE 1-continued

| Test data of storage stability | | | | | | |
|---|---|---|---|---|---|---|
| | Initial Indicator | | | After Storage at 50° C. for One Month | | |
| Sample | Viscosity (25° C. mPa · s) | NCO (%) | Color No. | Viscosity (25° C. mPa · s) | NCO (%) | Color No. |
| Example 12 | 3800 | 20.59 | 4 | 3700 | 20.57 | 4 |
| Example 13 | 7700 | 17.20 | 17 | 7900 | 17.12 | 21 |
| Comparative Example 1 | 5900 | 19.50 | 61 | 6500 | 19.32 | 97 |
| Comparative Example 2 | 5300 | 19.44 | 82 | 5800 | 19.22 | 123 |
| Comparative Example 3 | 6400 | 19.31 | 96 | 7300 | 19.05 | 140 |

It can be seen from Examples 1-13 and Comparative Examples 1-3 that, in the presence of cyclohexylamine with the content described in the present application, the prepared hydrophilic sulfonic acid-modified polyisocyanate has lower color number and better storage stability, and shows non-obvious color change after storage at a certain temperature.

What is claimed is:

1. A sulfonic acid-modified polyisocyanate, which is a reaction product obtained from a reaction comprising the following components:

a) at least one polyisocyanate component;

b) at least one organic compound with one or more of a sulfonic acid group and/or a sulfonate group, wherein the compound contains at least one of a mercapto group, a primary amino group or a secondary amino group;

c) at least one tertiary amine;

d) at least one cyclohexylamine with the following structure:

;

wherein, $R_1$ is one of cyclohexyl, cyclohexylmethyl, p-methylcyclohexyl, 2-methylcyclohexyl, 2,3-dimethylcyclohexyl, 3,3,5-trimethylcyclohexyl or 4-tert-butylcyclohexyl, and $R_2$ is hydrogen or a saturated or unsaturated, linear or branched, aliphatic or alicyclic or aromatic organic group having 1 to 18 carbon atoms wherein based on a mass of the component a) being 1000 parts, a mass of the component d) added is 0.05-2 parts.

2. The sulfonic acid-modified polyisocyanate according to claim 1, wherein, based on a mass of the component a) being 1000 parts, a mass of the component b) added is 5-150 parts.

3. The sulfonic acid-modified polyisocyanate according to claim 1, wherein a molar ratio of the component c) to the component b) is 0.5-1.5:1.

4. The sulfonic acid-modified polyisocyanate according to claim 1, wherein the component a) of polyisocyanate is one or more of an aliphatic polyisocyanate, a alicyclic polyisocyanate, an araliphatic polyisocyanate and/or an aromatic polyisocyanate, or a modified polyisocyanate, which has an average isocyanate functionality of 2.0-5.0 and an NCO content of 7.0-32.0 wt %.

5. The sulfonic acid-modified polyisocyanate according to claim 1, wherein the polyisocyanate component is an aliphatic, alicyclic, araliphatic or aromatic diisocyanate which has a molecular mass of 100-500.

6. The sulfonic acid-modified polyisocyanate according to claim 1, wherein the component b) is a sulfonic acid and/or a sulfonate, which has an amino group.

7. The sulfonic acid-modified polyisocyanate according to claim 6, wherein the component b) is a sulfonic acid organic compound with a secondary amino group, which has the following structure:

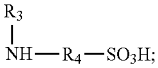

;

wherein $R_3$ is one of cyclohexyl, cyclohexylmethyl, p-methylcyclohexyl, 2-methylcyclohexyl, 2,3-dimethylcyclohexyl, 3,3,5-trimethylcyclohexyl or 4-tert-butylcyclohexyl, and $R_4$ is a linear or branched aliphatic group having 2 to 6 carbon atoms.

8. The sulfonic acid-modified polyisocyanate according to claim 1, wherein the tertiary amine c) is an acyclic and/or cyclic tertiary amine substituted with an aliphatic and/or alicyclic group.

9. The sulfonic acid-modified polyisocyanate according to claim 1, wherein a catalyst, conventionally used in the polyurethane field, is further added in the modified polyisocyanate to mix with the tertiary amine c) for use, such as an organometallic catalyst: one or a mixture of at least two of aluminium tris (ethyl acetoacetate), tin n-octoate, zinc n-octoate, tin (II) 2-ethyl-1-hexanoate, dibutyltin (IV) dichloride, dibutyltin (IV) diacetate, dibutyltin (IV) dilaurate, dioctyltin (IV) diacetate or molybdenum glycolate.

10. The sulfonic acid-modified polyisocyanate according to claim 1, wherein the component d) of cyclohexylamine is one or more of cyclohexylamine, cyclohexanemethylamine, p-methylcyclohexylamine, 2-methylcyclohexylamine, 2,3-dimethylcyclohexylamine, 3,3,5-trimethylcyclohexylamine, 4-tert-butylcyclohexylamine, N-methylcyclohexylamine, N-methyl-cyclohexylmethylamine, N,4-dimethylcyclohexan-1-amine, N-methyl-2-methylcyclohexylamine, N-methyl-2,3-dimethylcyclohexylamine, N-methyl-3,3,5-trimethylcyclohexylamine, N-methyl-4-tert-butylcyclohexylamine, N-ethylcyclohexylamine, N-ethyl-methylcyclohexylamine, N-ethyl-p-methylcyclohexylamine, N-ethyl-2-methylcyclohexylamine, N-ethyl-2,3-dimethylcyclohexylamine, N-ethyl-3,3,5-trimethylcyclohexylamine and N-ethyl-4-tert-butylcyclohexylamine.

11. A preparation method of the sulfonic acid-modified polyisocyanate according to claim 1, comprising reacting the component a) of polyisocyanate component, the component b) and the component d) at 70-110° C. in the presence of the component c) of tertiary amine, wherein the component a) of polyisocyanate is fed in one or more steps.

12. The preparation method according to claim 11, wherein an antioxidant is added in the preparation method.

13. The preparation method according to claim 11, wherein the antioxidant is an aromatic amine, a hindered phenol, and a derivative thereof, which can scavenge free radicals, or a phosphorus-containing or sulfur-containing organic compound which can enable the decomposition of hydroperoxides, or a combination thereof.

14. The preparation method according to claim 11, wherein the reaction is carried out in a solvent which is inert to reacting with NCO.

15. The preparation method according to claim 14, wherein the solvent which is inert to reacting with NCO comprises one or a mixture of at least two of acetone, butanone, ethyl oxocyclopentylacetate, butyl acetate, N-ethylpyrrolidone, N-methylpyrrolidone, toluene, xylene, chlorobenzene, propylene glycol methyl ether acetate, 1-methoxyprop-2-yl acetate, 3-methoxy-n-butyl acetate, an aromatic compound, dimethyl carbonate, diethyl carbonate, butyrolactone, caprolactone and methyl caprolactone.

16. The sulfonic acid-modified polyisocyanate according to claim 1, wherein the polyisocyanate component is tetramethylene diisocyanate, pentamethylene diisocyanate, hexamethylene diisocyanate, dodecamethylene diisocyanate, 1,4-cyclohexane diisocyanate, isophorone diisocyanate, 4,4'-dicyclohexylmethane diisocyanate, 4,4'-dicyclohexylpropane diisocyanate, 1,4-phenylene diisocyanate, 2,4-toluene diisocyanate, 2,6-toluene diisocyanate, 4,4'-diphenylmethane diisocyanate, 2,2'-diphenylmethane diisocyanate, 2,4'-diphenylmethane diisocyanate, tetramethyl-xylylene diisocyanate and p-xylylene diisocyanate, or a mixture of the diisocyanates.

17. The sulfonic acid-modified polyisocyanate according to claim 1, wherein the polyisocyanate component is a modified polyisocyanate with an isocyanurate group based on one or more of 1,6-hexamethylene diisocyanate, isophorone diisocyanate and 4,4'-dicyclohexylmethane diisocyanate.

18. The sulfonic acid-modified polyisocyanate according to claim 1, wherein the component b) is a sulfonic acid and/or a sulfonate, which has a secondary amino group.

19. The sulfonic acid-modified polyisocyanate according to claim 1, wherein the tertiary amine c) is one or more of trimethylamine, triethylamine, tripropylamine, N,N-dimethylbutylamine, N,N-diethylmethylamine, N,N-diisopropylethylamine, N,N-dimethylcyclohexylamine, N-methylpiperidine, N-methylquinoline, N-ethylquinoline and/or N-ethylmorpholine.

20. The sulfonic acid-modified polyisocyanate according to claim 1, wherein the component d) of cyclohexylamine contains cyclohexylamine having the same group as $R_3$ in the component b) of organic compound.

* * * * *